United States Patent [19]

Michel

[11] 4,205,174
[45] May 27, 1980

[54] PROCESS FOR THE PRODUCTION OF 6-SUBSTITUTED 4-METHYL-2-PYRIDONES

[75] Inventor: Urs Michel, Visp, Switzerland

[73] Assignee: Lonza Ltd., Basel, Switzerland

[21] Appl. No.: 2,594

[22] Filed: Jan. 11, 1979

[30] Foreign Application Priority Data

Jan. 11, 1978 [CH] Switzerland ............................ 272/78

[51] Int. Cl.² .......................................... C07D 213/64
[52] U.S. Cl. .................................................. 546/249
[58] Field of Search ........................................ 546/249

[56] References Cited

U.S. PATENT DOCUMENTS

| 2,516,673 | 7/1950 | Bruce | 260/295.5 |
| 3,711,488 | 1/1973 | Bayer | 546/249 |
| 3,754,088 | 8/1973 | Witzel | 424/267 |
| 3,926,935 | 12/1975 | Rogers et al. | 260/96.5 R |

FOREIGN PATENT DOCUMENTS

| 643891 | 8/1964 | Belgium . |
| 2414608 | 10/1973 | Fed. Rep. of Germany . |
| 2363513 | 7/1975 | Fed. Rep. of Germany . |
| 2210409 | 7/1974 | France . |
| 851033 | 10/1960 | United Kingdom . |

OTHER PUBLICATIONS

Chem. Abs., vol. 73 (1970) 120508a, abstracting South African Patent No. 69/06,039.
I. Alkonyi, Report 98, (1965) pp. 3099–3101.
Morrison, Robert T. et al., "Organic Chemistry", Allyn and Bacon, Inc. Boston (1956) pp. 23–24.
Robertson, G. Ross et al., "Laboratory Practice of Organic Chemistry", 4th Ed., The Macilllan Company, New York, (1962) p. 272.

*Primary Examiner*—Norma S. Milestone

*Attorney, Agent, or Firm*—Fisher, Christen & Sabol

[57] ABSTRACT

Process for the production of 6-substituted-4-methyl-2-pyridones having the formula:

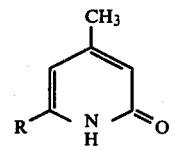

wherein R is a branched or unbranched alkyl group, a halogenated branched or unbranched alkyl group or a substituted or unsubstituted aryl group. Senecioic acid amide having the formula:

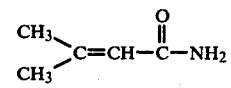

is reacted in a solvent at an elevated temperature in the presence of a Lewis acid (as a catalyst) with an acyl chloride having the formula:

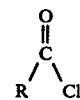

wherein R has the same meaning as above. The reaction mixture is subsequently placed in an aqueous phase for hydrolysis. The 6-substituted-4-methyl-2-pyridone is separated by extraction through the buffering of the reaction mixture at a pH of 4 to 5.

17 Claims, No Drawings

PROCESS FOR THE PRODUCTION OF 6-SUBSTITUTED 4-METHYL-2-PYRIDONES

BACKGROUND OF THIS INVENTION

1. Field of this Invention

This invention relates to the production of 6-substituted-4-methyl-pyridones.

2. Prior Art 2-pyrones have been reacted with ammonia or its salts in the presence of amines, especially substituted aminopyridines or imiazoles, to produce the corresponding 2-pyrones—see German OS 2,214,608. It is known to acylate α,β-unsaturated carboxylic acid esters, for example, β,β-dimethyl-acrylic acid-ethyl ester, into δ-oxo-β-methyl-Δ$^{α,β}$-hexonic acid ethyl ester in the presence of AlCl$_3$ with acetyl chloride (see I. Alkonyi, Report 98, 3099 (1965). The cyclization of the unsaturated δ-ketoacid ester with acidic or basic catalysts into the corresponding pyrones are known from Belgian Pat. No. 643,891. Furthermore, it is known from South African Pat. No. 6,906,039 to react unsaturated δ-keto ester with amines to produce 2-pyridones or from English Pat. No. 851,033 to react pyrones with amines into analogous pyridones. Such processes, however, are in most instances uneconomical for the production of 2-pyridones because of the expensive educts or because the method of processing is too complex. Other processes, in turn, may not simply be transferred to and modified for the production of 2-pyridones.

According to the Lewis definition, an acid is a substance that can take up an electron pair to form a covalent bond. Thus an acid is an electron pair acceptor. See pages 23 and 24 of Morrison, Robert T., et al., "Organic Chemistry", Allyn and Bacon, Inc., Boston, (1959). A proton is an acid because it is deficient in electrons, and needs an electron pair to complete its valence shell. Hydroxide ion, ammonia, and water are bases because they contain electron pairs available for sharing. In boron trifluoride, BF$_3$, boron has only six electrons in its outer shell and hence tends to accept another pair to complete its octet. Boron trifluoride is an acid and combines with such bases as ammonia or ethyl ether. Aluminum chloride, AlCl$_3$, is an acid, and for the same reason. In stannic chloride, SnCl$_4$, tin has a complete octet but can accept additional pairs of electrons (e.g., in SnCl$_6^{--}$) and hence it is an acid, too. In speaking about this kind of acid, the expression Lewis acid, or sometimes acid in the Lewis sense, is used. To be acidic in the Lewis sense, a molecule must be electron-deficient; in particular, one looks for an atom bearing only a sextet of electrons.

Robertson, G. Ross, et al., "Laboratory Practice of Organic Chemistry", 4th Ed., The Macmillan Company, New York, (1962), page 272, says that Lewis acids are catalysts. When an alkyl halide is treated with anhydrous aluminum chloride, the strongly electrophilic aluminum compound attracts a fourth electron-rich halogen atom to complete a group of four electron pairs, to form AlCl$_4^-$. Such possible reaction becomes feasible if the positive alkyl radical, about to be left behind, simultaneously has the opportunity to attack another electron-rich compound such as benzene. In the present example, benzyl benzene, or diphenylmethane is produced. Although the reagent benzyl chloride contains a benzene ring, its reactive zone is outside the ring and it qualifies here as an "alkyl" derivative. Since aluminum chloride (the Lewis acid) is regenerated, it may be termed a catalyst. An acid anhydride may be substituted for the alkyl halide. By catalytic action of the aluminum chloride, one of the carbonyl groups of the anhydride is set free, ready to attack benzene as the alkyl group did in the previous example. An aromatic keto acid results, such as the β-benzolypropionic acid.

Lewis classed boron chloride as an acid and defined an acid as a substance which can fill the valence shell of one of its atoms with an unshared pair of electrons from another molecule. In favor of this concept is the fact that substances such as boron fluoride, aluminum chloride, zinc chloride or stannic chloride can catalyze the same types of reaction, for example, polymerization of olefins or the formation of ethers, as can a proton. Such compounds often are called Lewis acids. With this definition of an acid, it should be remembered that hydrogen chloride, sulfuric acid, acetic acid, and in fact any of the countless number of substances that from the beginning of chemistry have been called acids, are not acids under the Lewis definition. The acid as defined by Lewis is the bare unsolvated proton, which is practically incapable of existence. Moreover, substance such as cupric ion, which seldom are considered as acids, are acids in the Lewis sense, because they can fill their valence shell with unshared pairs from other molecules, as when cupric ion reacts with ammonia molecules to give the cupricammonia complex ion. Instead of calling all types of compounds capable of accepting a pair of electrons acids, Sidwick in his book on valency published in 1927 called them electron-acceptors, thus leaving the term acid for those compounds capable of transferring a proton to a base. Perhaps a better term than electron-acceptor for reagents, such as, boron fluoride, aluminum chloride, stannic chloride, or zinc chloride that behave like a proton would be protonoid or protonoid reagent. This term would imply properties similiar to those of a proton but would not group these compounds with the substances commonly called acids. See page 235 of Noller, Carl R., "Chemistry of Organic Compounds", W. B. Saunders Company, Philadelphia, (1951).

BROAD DESCRIPTION OF THIS INVENTION

An object of this invention is to provide a process for the production of 6-substituted-4-methyl-2-pyridones having the formula:

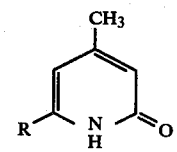

wherein R is an unbranched or branched alkyl group, a halogenated branched or unbranched alkyl group or a substituted or unsubstituted aryl group. Other objects and advantages of this invention are set out herein or obvious herefrom to one ordinarily skilled in the art.

The process of this invention achieves the objects and advantages of this invention.

This invention involves a process for the production of 6-substituted-4-methyl-2-pyridones having the formula:

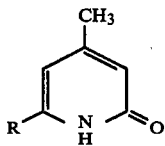

wherein R is a branched alkyl group, an unbranched alkyl group, a halogenated branched alkyl group, a halogenated unbranched alkyl group, a substituted aryl group or an unsubstituted aryl group. The process involves reacting sececioic acid amide, which has the formula:

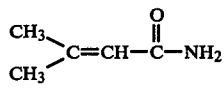

in a solvent at an elevated temperature in the presence of a Lewis acid, as the catalyst, with an acyl chloride having the formula:

wherein R has the same meaning as above. The reaction mixture subsequently is inserted into an aqueous phase for hydrolysis. The resultant 6-substituted-4-methyl-2-pyridone is separated by extraction through the buffering of the reaction mixture at a pH of 4 to 5.

The Lewis acid is preferably a metal halide and is most preferably aluminum chloride. Preferably 2 to 3 equivalents of catalyst (Lewis acid) are used per one equivalent of senecioic acid amide. The solvent is preferably carbon disulfide or a chlorinated hydrocarbons and is most preferably methylene chloride. The acyl chloride is preferably one where R is an aliphatic radical with 2 to 4 carbon atoms. Most preferably the acyl chloride is acetyl chloride, chloroacetyl chloride, propionyl chloride, butyryl chloride, isobutyryl chloride or benzoyl chloride.

The process of this invention produces the 6-substituted-4-methyl-2pyridones in a simple manner, with high purity and with high yield.

The compounds produced according to this invention can, for example, be used as an educt for the production of pyridoxinic analogous derivatives (see U.S. Pat. No. 2,516,673) or as complexes in the form of the N-alkyl compound as anti-coccidiostatica (see French Pat. No. 2,210,409 and U.S. Pat. No. 3,926,935). The tetrahydro derivative of 4,6-dimethyl-pyridone-(2), easily reproducible by hydrogenation, has a pharmacological effect (see U.S. Pat. No. 3,754,088). An N-methacrylic acid derivative can be used in photography (see German OS No. 2,363,513).

DETAILED DESCRIPTION OF THIS INVENTION

As used herein, senecioic acid amide is $\beta,\beta$-dimethylacrylic acid amide.

The process according to this invention is carried out so that the catalyst together with the solvent and the senecioic acid amide is brought to reflux temperature (preferably) in a reaction vessel while stirring. But other reaction temperatures can be used.

Lewis acids, which are preferably metal halides, is a catalyst as used in this invention. As used herein halide includes F, I, Cl and Br. The most preferred Lewis acid is $MgBr_2$, $MgCl_2$, $MgI_2$, $MgF_2$, $PCl_3$, $SiCl_4$, $SnCl_4$, $HgCl_2$, $ZnCl_2$, $CuCl_2$, $FeCl_3$, $AuBr_3$, $AgCl$, $TiCl_4$, $AmCl_3$, $AmBr_3$, $SbBr_3$, $SbCl_3$, $MoCl_3$, $BiCl_3$, $CdCl_2$, $CdBr_2$, $CaCl_3$, $PbBr_2$, $PbCl_2$, $AlBr_3$, $AlF_3$, $AlI_3$, $BCl_3$, $BF_3$, $BI_3$, $WCl_4$, $CaCl_3$, $CsCl$, $CoCl_2$, $CoCl_3$, $LiCl$, $NaCl$, $ZrCl_2$, $FeBr_2$, $FeBr_3$, $FeCl_2$, $FeF_3$, $KCl$, $SeCl_4$, $CuCl$, $CrCl_2$, $CrCl_3$, $AuCl_3$, $PtCl_2$, $TiCl_4$, $VCl_2$, $MnCl_2$, $MnCl_3$, $NiCl_2$, $PdCl_2$, $PtCl_3$, $CuBr_2$, and $SrCl_2$. Mixtures of Lewis acids can be used.

Suitable solvents include carbon disulfide and chlorinated hydrocarbons. The most preferred solvent is methylene chloride. Suitable chlorinated and fluorinated aliphatic hydrocarbon solvents are brominated 1,1-dichloroethane, carbon tetrachloride, chloroform, ethylene chloride, 1,1,2,2-tetrachloroethane, 1,1,1-trichloroethylane, cis-dichloroethylene, trans-dichloroethylane, pentachloroethane, tetrafluoroethane, hexachloroethane, tetrabromoethane, chlorodifluoromethane, trichlorofluoromethane, fluoropentachloroethane, pentachloroethane, 1-chloro-2-fluoroethane, bromodichloromethane, 1,2-dichloroethane, iodoethane, 1,1,2-trichloroethane, bromochloroethane, 1,1,1-trichloro-2,2,2-trifluoroethane, 1,1,2-trichloro-1,2,2-trifluoroethane, 1-bromoethane, ethylene bromide, iodomethane, 1-bromo-2-fluoroethane, 1-bromo-2-chloroethane, bromotrichloromethane, chlorodibromomethane, chloroiodomethane, dibromomethane, dibromofluoromethane, fluoroiodomethane, 1-bromopropane, 2-bromopropane, 2-bromo-2-chloropropane, 1-bromo-3-fluoropropane, 1-chloropropane, 1-chloro-3-fluoropropane, 2-bromobutane, 1,1-dichloropropane, 1,2-dichloropropane, 2,2-dichloropropane, isopropyl iodide, 1-bromobutane, 1-chlorobutane, 2-chlorobutane, heptachlorobutane, pentachlorobutane, 1,2,3,3-tetrachlorobutane, 2-chloropentane and 1,3-dichloropentane. The solvent needs to be liquid at the reaction temperature (usually reflux temperature). The senecioic acid, solvent and Lewis acid should be anhydrous.

Preferably 2 to 3 equivalents of catalyst (Lewis acid) are used per equivalent of senecioic acid amide. The quantity of solvent used is not critical.

The acyl chloride is preferably added to the reaction mixture mentioned while stirring. 1 to 1.2 moles of acyl chloride is preferably used per mole of senecioic acid amide.

R in the acyl chloride can be an unbranched alkyl group, a branched alkyl group, a halogenated branched alkyl group or an unbranched alkyl group. Preferably any alkyl group used for R has 2 to 4 carbon atoms. Preferably the acyl chloride is acetyl chloride, chloracetyl chloride, propionyl chloride, butyryl chloride or isobutyryl chloride. Other examples are $BrClCHCOCl$, $BrCH_2COCl$, $BrFCHCOCl$, $Cl_2CHCOCl$, $Br_2CHCOCl$, $I_2CHCOCl$, $F_2CHCOCl$, $FCH_2COCl$, $Cl_3COCl$, $CH_3CHBrCOCl$, $CH_3CHClCOCl$, $ClCH_2CH_2COCl$, $ClCH_2CHClCOCl$, $Cl_2CHCH_2COCl$, $FCH_2CH_2COCl$, $CH_3CH_2CHBrCOCl$, $ClCH_2CH_2CH_2COCl$, and $Cl(CH_2)_4COCl$.

R is the acyl chloride can be a substituted aryl group or an unsubstituted aryl group (preferably benzoyl chloride). When R is benzyl, it can be substituted for example, with one or more halogens (e.g., Cl, F, Br and I).

Examples are 2-bromo-benzoyl chloride and 3-chlorobenzoyl chloride.

After about 6 to 24 hours of boiling at the reflux temperature, the reaction is complete and the reaction mixture is put into an aqueous phase for the purpose of hydrolysis. The hydrolyzed reaction mixture is subsequently mixed with a solution of buffer salts. Any suitable buffer can be used.

The ampholytic 2-pyridone is water soluble both in a strongly alkaline medium and, in the case of the use of AlCl₃ catalysts, the gel-like precipitated aluminum hydroxide makes an isolation of the 2-pyridone impossible in a neutral to weakly alkaline medium. Since hydrolysis with water must take place because of the separation of the aluminum chloride, the strongly acid reaction solution is buffered off with 3 equivalents of sodium acetate per equivalent of AlCl₃ as well as with 1 equivalent of NaOAc/equivalent of liberated HCl. In this way, a reaction mixture with a pH of 4 to 5 is obtained in all cases, which corresponds approximately to the isoelectric point of the pyridone, hence at the most optimal extraction conditions.

To repeat, one can produce a 6-substituted-4-methyl-2-pyridone by conversion of senecioic acid amide in the presence of a Lewis acid as a catalyst with an acyl chloride, followed by subsequent hydrolysis in an aqueous phase and separation from the reaction mixture buffered to a pH of 4.5.

EXAMPLE 1

4,6-dimethyl-pyridone-(2)

18.8 g (0.141 mole) of anhydrous aluminum chloride was mixed with 50 ml of methylene chloride (absolute) and 4.67 g (0.04 mole) of senecioic acid amide. The reaction mixture was heated to reflux temperature. Then 3.68 g (0.047 mole) of acetyl chloride in 10 ml of methylene chloride (absolute) was added drop by drop within 30 minutes. The reaction mixture was boiled on the reflux for another 24 hours and then allowed to cool. The reaction mixture was added drop by drop while stirring into a mixture of 50 ml of methylene chloride and 50 ml of water. After that, a solution of 38.6 g (0.47 mole) of sodium acetate (anhydrous) in 75 ml of water was added. The pH of the solution (reaction mixture) was 4.6. The organic phase was separated in a separating funnel and the aqueous phase was extracted with chloroform. The organic phases were combined, dried with sodium sulfate (sicc.) and evaporated (boiled down). After drying, 5.63 g of raw product was obtained. After recrystallization of the raw product from acetone (absolute), 3.93 g of white crystals having a melting point of 179.9° to 180.2° C. was obtained. The yield amounted to 3.93 g of 4.6-dimethyl-pyridone having a content of 98.5 percent—this corresponded to a yield of 67 percent, related to the senecioic acid amid used.

EXAMPLE 2

6-isopropyl-4-methyl-pyridone-(2)

The procedure of Example 1 was repeated, except that, instead of acetyl chloride, 5 g (0.047 mole) of isobutyryl chloride was used. After 16 hours of boiling on the reflux, the hydrolysis was carried out as in Example 1. The pH value was 4.5. After extraction of the aqueous phase with methylene chloride, the organic phase was dried and subsequently evaporated to dryness. 6.98 g of raw product was obtained. After recrystallization of the raw product in 15 ml of cyclohexane and 5 ml of acetic acid ethyl ester, 5.5 g of product having a melting point of 149.5° to 149.6° C. was obtained. The 5.5 g of 6-isopropyl-4-methyl-pyridone-(2) had a content (purity) of 99 percent, which corresponded to a yield of 77 percent, related to the senecioic acid amide used.

EXAMPLE 3

6-chloromethyl-4-methyl-pyridone-(2)

18.8 g (0.141 mole) of aluminum chloride (anhydrous) was mixed with 50 ml of methylene chloride (absolute) and 4.69 g (0.047 mole) of senecioic acid amide. The reaction mixture was heated to reflux temperature. Then 5.31 g (0.047 mole) of chloroacetyl chloride in 10 ml of methylene chloride (absolute) was added drop by drop. The reaction mixture was boiled for 24 hours on the reflux. Then hydrolization was achieved by introduction of the reaction mixture into a mixture of 50 ml of methylene chloride and 50 ml of water. After adding a solution of 38.6 g of sodium acetate (anhydrous) in 75 ml of water, the pH was 4.4. The organic phase was separated and the aqueous phase was treated altogether with 70 ml of methylene chloride. The organic phases were combined and dried, and the solvent was evaporated off. 4.02 g of raw product was obtained. By evaporation of the aqueous phase, drying and extraction with 300 ml of acetone (absolute) after evaporation, an additional 2.85 g of raw product was obtained. The entire quantity of raw product was recrystallized from acetonitrile. 4.16 g of 6-chloromethyl-4-methyl-pyridone-(2), having a purity of 99 percent and a melting point of 162.8° to 162.9° C., was obtained. This corresponded to a yield of 56 percent, related to the senecioic acid amide used.

EXAMPLE 4

6-phenyl-4-methyl-pyridone-(2)

The procedure of Example 2 was repeated, except that, instead of chloroacetyl chloride, 6.61 g (01047 mole) of benzoyl chloride was used. The recrystallization of the 9.52 g of raw product was accomplished from 20 ml of ethanol, whereby 5.53 g of 6-phenyl-4-methyl-pyridone-(2), having a melting point of 181.6° to 182.0° C. was obtained. The product had a purity of 99.2 percent—this corresponded to a yield of 63.5 percent, related to the senecioic acid amide used.

What is claimed is:

1. Process for the production of a 6-substituted-4-methyl-2-pyridone having the formula:

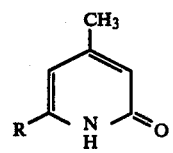

wherein R is a branched alkyl group, an unbranched alkyl group a halogenated branched alkyl group, an halogenated unbranched alkyl group, a substituted aryl group or an unsubstituted aryl group, characterized in that: (a) senecioic acid amide having the formula:

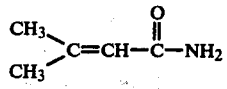

is reacted in a solvent at an elevated temperature in the presence of a Lewis acid, as the catalyst, with an acyl chloride having the formula:

wherein R has the same meaning as above, (b) the resultant reaction mixture is inserted into an aqueous phase, whereby hydrolysis occurs, and (c) the 6-substituted-4-methyl-2-pyridione is separated by extraction through the buffering of the reaction mixture at a pH of 4 to 5.

2. Process as claimed in claim 1 wherein said Lewis acid is a metal halide.

3. Process as claimed in claim 2 wherein said metal halide is aluminum chloride.

4. Process as claimed in claim 2 wherein said solvent is carbon disulfide or a chlorinated hydrocarbon.

5. Process as claimed in claim 1 wherein said high temperature is reflux temperature.

6. Process as claimed in claim 5 wherein said reflux temperature is held for about 6 to about 24 hours.

7. Process as claimed in claim 1 wherein 1 to 1.2 mole of said acyl chloride is used per mole of senecioic acid amide.

8. Process as claimed in claim 1 wherein said solvent is carbon disulfide or a chlorinated hydrocarbon.

9. Process as claimed in claim 8 wherein said solvent is a chlorinated hydrocarbon.

10. Process as claimed in claim 9 wherein said chlorinated hydrocarbon is methylene chloride.

11. Process as claimed in claim 10 wherein said reaction mixture in step (c) is buffered to a pH of about 4.5.

12. Process as claimed in claim 1 wherein 2 to 3 equivalents of said Lewis acid is used per equivalent of senecioic acid amide.

13. Process as used in claim 12 wherein 1 to 1.2 mole of said acyl chloride is used per mole of senecioic acid amide.

14. Process as claimed in claim 1 wherein R in said acyl chloride is an aliphatic radical having 2 to 4 carbon atoms.

15. Process as claimed in claim 14 wherein 1 to 1.2 mole of said acyl chloride is used per mole of senecioic acid amide.

16. Process as claimed in claim 1 wherein said Lewis acid is aluminum chloride and the buffer used to buffer the reaction solution is about 3 equivalents of sodium acetate per one equivalent of aluminum chloride.

17. Process as claimed in claim 1 wherein said acyl chloride is acetyl chloride, chloracetyl chloride, propionyl chloride, butyryl chloride, isobutyryl chloride or benzoyl chloride.

* * * * *